(12) United States Patent
Neal

(10) Patent No.: US 8,605,925 B2
(45) Date of Patent: Dec. 10, 2013

(54) ACOUSTIC PROCESSING METHOD AND APPARATUS

(75) Inventor: Timothy Neal, West Ryde (AU)

(73) Assignee: Cochlear Limited, Macquarie University, NSW (AU)

( * ) Notice: Subject to any disclaimer, the term of this patent is extended or adjusted under 35 U.S.C. 154(b) by 94 days.

(21) Appl. No.: 12/995,416

(22) PCT Filed: May 29, 2009

(86) PCT No.: PCT/AU2009/000686
§ 371 (c)(1),
(2), (4) Date: Feb. 16, 2011

(87) PCT Pub. No.: WO2009/143588
PCT Pub. Date: Dec. 3, 2009

(65) Prior Publication Data
US 2011/0135129 A1 Jun. 9, 2011

(30) Foreign Application Priority Data
May 30, 2008 (AU) ................................ 2008902723

(51) Int. Cl.
*H04R 25/00* (2006.01)
(52) U.S. Cl.
USPC .......................................... 381/320; 381/312
(58) Field of Classification Search
USPC .............................. 381/312, 317, 320, 321, 57
See application file for complete search history.

(56) References Cited

U.S. PATENT DOCUMENTS

| 4,630,305 | A | | 12/1986 | Borth et al. | |
|---|---|---|---|---|---|
| 4,641,344 | A | * | 2/1987 | Kasai et al. | 381/57 |
| 6,151,400 | A | | 11/2000 | Seligman | |
| 6,757,395 | B1 | | 6/2004 | Fang et al. | |
| 7,072,717 | B1 | * | 7/2006 | Wolf et al. | 607/57 |
| 7,783,063 | B2 | * | 8/2010 | Pocino et al. | 381/119 |
| 2003/0035549 | A1 | * | 2/2003 | Bizjak et al. | 381/56 |

FOREIGN PATENT DOCUMENTS

| EP | 0326905 | 8/1989 |
|---|---|---|
| WO | 02/084866 | 10/2002 |

OTHER PUBLICATIONS

Extended European Search Report, European Application No. 09753352.5 mailed Feb. 15, 2013 (7 pages).
International Search Report, for PCT/AU2009/000686, mailed Sep. 4, 2009, 2 pages.
Written Opinion, for PCT/AU2009/000686, mailed Sep. 4, 2009, 6 pages.

\* cited by examiner

*Primary Examiner* — Brian Ensey
*Assistant Examiner* — Norman Yu
(74) *Attorney, Agent, or Firm* — Kilpatrick, Townsend & Stockton, LLP

(57) ABSTRACT

A processing method and apparatus for reducing noise in an auditory prosthesis, for example a hearing aid or cochlear implant, are disclosed. The noise floor of the input sound signal is estimated, and the base output level of the output signal is moved in response, in a preferred form to substantially the estimated noise floor level, without modifying the maximum output level. This has the effect of maximising the dynamic range of the user in response to the target sound signal.

21 Claims, 9 Drawing Sheets

ACOUSTIC PROCESSING METHOD AND APPARATUS

CROSS-REFERENCE TO RELATED APPLICATION

The present application is a National Stage application of PCT/AU2009/000686 entitled "Acoustic Processing Method and Apparatus", filed on May 29, 2009, which claims priority from Australian Provisional Patent Application No. 2008902723, filed on May 30, 2008, which are hereby incorporated by reference herein.

BACKGROUND

1. Field of the Invention

The present application relates to processing audio signals containing noise, particularly for auditory prostheses.

2. Related Art

Auditory prostheses include any acoustic or electrical auditory prostheses, such as hearing aids, bone anchored hearing aids, middle ear implants, intracochlear implants, brain stem implants, implanted acoustic prostheses or any combination of these, for example prostheses providing combined electrical and acoustic stimulation. For those prostheses having an external part and an implanted part, the external part may be continuously, intermittently or occasionally in communication with the implanted part.

Auditory prostheses require, as an input, an electrical signal corresponding to an audio signal for processing in the device. This input is most commonly provided by a microphone. For example, a conventional cochlear implant consists of an external part containing a microphone, a sound processor and a transmitter, and an internal part which contains a receiver/stimulator device and an electrode array. Sound enters the microphone, which outputs a corresponding electrical signal to the sound processor, which in turn codes the sound using one of many possible processing strategies. The coded signal is passed to the transmitter, which sends it to the implanted receiver/stimulator unit. The receiver/stimulator then sends the corresponding stimuli to the appropriate electrodes, so as to provide a percept of hearing for a user.

A significant problem for users of auditory prostheses is listening to a target signal in the presence of noise, such as when talking on the phone, or in restaurants, sports stadiums, supermarkets, and the like. One major source of this problem is that a hearing impaired person has a much smaller range of perceivable sounds than a normal hearing person. This perceivable range of sounds is known as the dynamic range.

One way existing systems combat this problem is by automatically turning down the gain of the system in the presence of noise. By turning down the gain of the system the processor can lower the noise level such that it is mapped to the lower end of the recipient's dynamic range. An example of such an algorithm is disclosed in U.S. Pat. No. 6,151,400, and reproduced in part as FIG. 10.

The problem with such algorithms is that while they turn down the noise level, they also turn down the level of the target signal. This means that while the user may hear less noise, the target signal also becomes more difficult to hear.

SUMMARY

In a broad form, the present invention provides a method and apparatus for rescaling the signal for an auditory prosthesis in order to optimise the dynamic range available to the user.

According to a first aspect of the present invention, there is provided a method for processing an input sound signal by an auditory prosthesis comprising: performing a frequency analysis on the input sound signal to generate a plurality of analysis signals each corresponding to a channel within the input sound signal; applying a scaling function to each of the plurality of analysis signals in response to a control signal, such that for each channel, a minimum output level of the channel is modified in response to the control signal, while a maximum output level of the channel remains substantially unchanged; and applying stimulation to a recipient using at least one of the scaled signals.

According to a second aspect, there is provided a method for processing an input signal in an auditory prosthesis to produce an output signal, said output signal having a maximum output level and a minimum output level, said method including at least the steps of: estimating the noise floor of the input signal; applying a scaling function to the input signal such that the base level of the output signal is modified in response to the noise floor estimate, without substantially changing the maximum output level of the output signal; and applying stimulation to a recipient using at least one of the output signals.

According to a third aspect, there is provided an apparatus for processing a sound signal in an auditory prosthesis to produce an output signal, said output signal having a maximum output level and a base level, comprising: a noise floor estimator for estimating the noise floor of the sound signal; and a scaling circuit for applying a scaling function to the sound signal, such that a minimum output level of the output signal is modified in response to the noise floor estimate without substantially changing a maximum output level of the output signal.

According to a fourth aspect, there is provided a method for processing an input signal in an auditory prosthesis to produce an output signal, said method comprising processing said input signal so as to produce a set of channel input signals corresponding to frequency channels; for each channel, estimating the noise floor of the channel input signal; and applying a scaling function to the channel input signal to produce a channel output signal, the channel output signal having a base level and a maximum output level such that the base level of the channel output signal is modified in response to the noise floor estimate, while the maximum output level of the channel output signal remains substantially the same; and applying stimulation to a recipient using at least one of the output signals.

BRIEF DESCRIPTION OF THE DRAWINGS

An illustrative embodiment of the present invention will be described with reference to the accompanying figures, in which.

DETAILED DESCRIPTION

The present invention may be implemented in a variety of ways and the embodiments illustrated are to be considered only as illustrative constructions. For example, while the description below relates to cochlear implants, the present invention is also applicable to any auditory prosthesis, such as those listed above. The present invention is concerned specifically with the audio processing part of the signal path, it will be appreciated that the remaining aspects of the auditory prosthesis may be constructed and operated in any suitable way.

Figure 1C:
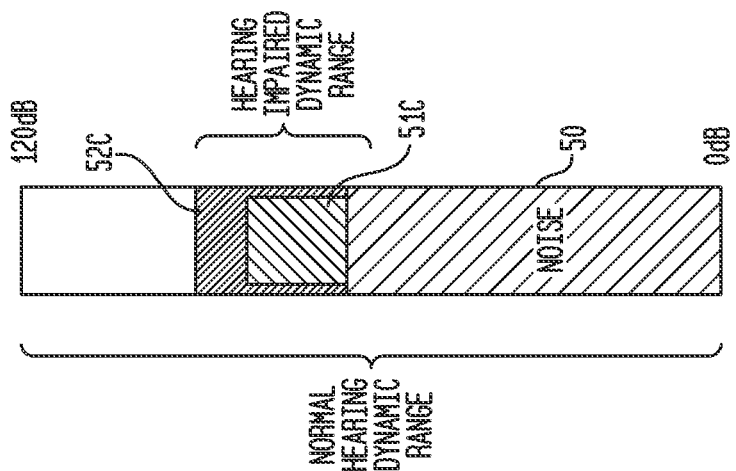
FIGS. 1a-c shows a schematic comparison of a signal in noise in a dynamic range between, respectively, a conventionally processed signal, a signal pre-processed with an automatic sensitivity control algorithm, and a signal processed using an embodiment of the present invention.
Figure 1B:
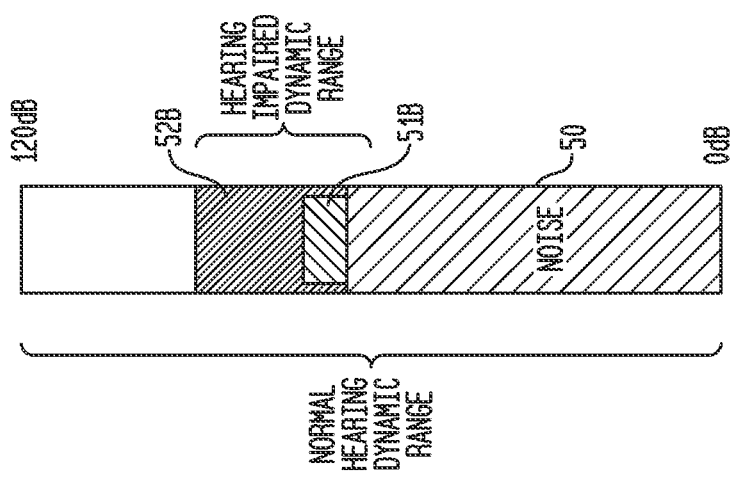
Figure 1A:
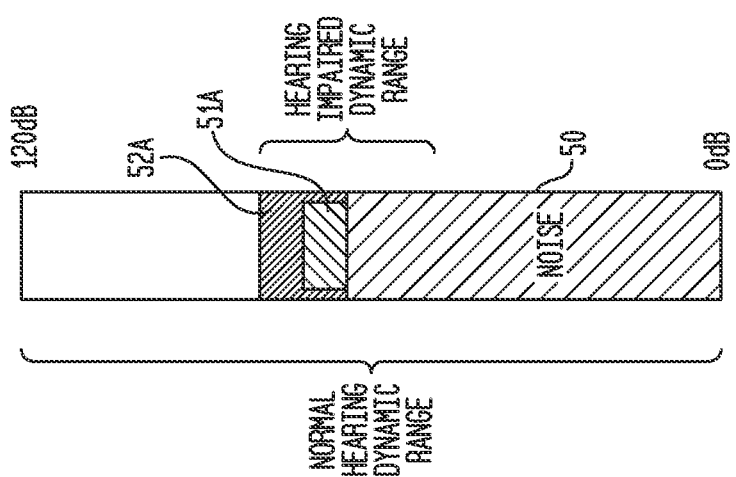

Shown in FIGS. 1*a-c* is a schematic comparison of an illustrative implementation of an embodiment of the present invention as compared to the unprocessed condition and as compared to the result of processing with the automatic sensitivity control (ASC) algorithm, as disclosed in U.S. Pat. No. 6,151,400 and herein incorporated by reference. In the three panes we see a comparison of the normal hearing dynamic range to the hearing impaired dynamic range 52A, 52B, 52C. Present in the environment is a noise source 50 and a target signal 51A, 51B, 51C.

In the unprocessed condition (FIG. 1A), the noise signal 50 fills much of the hearing impaired dynamic range 52A, and only a small region of the target signal 51A is presented to the listener.

FIG. 1B shows how the automatic sensitivity control alters the situation. In this case, the sensitivity of the system is decreased so that the noise 50 only enters the bottom of the dynamic range 52B of the hearing impaired listener. This has the detrimental side effect that the target signal 51 B is also reduced in level.

The effect of this implementation of the present invention, referred to as the automatic expander, is shown in FIG. 1C. Under this condition the noise 50 is still moved to the bottom of the dynamic range 52C, but the target signal 51 C above the noise 50 has been expanded to fill the dynamic range 52C. The effect of the automatic expansion algorithm is to keep the noise level at the bottom of the dynamic range while presenting signals above the noise closer to the level at which they are normally presented.

Figure 2:
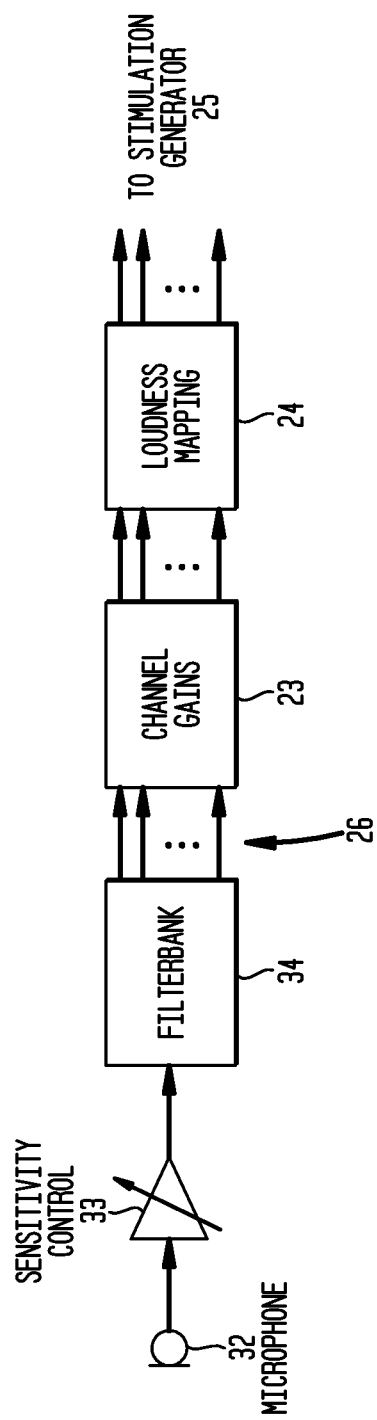
FIG. 2 shows a schematic view of a conventional cochlear implant signal path.

A simplified version of part of a known cochlear implant signal path is depicted in FIG. 2. A microphone 32 captures the acoustic signal and produces a corresponding electrical signal. The gain of this signal is adjusted by a sensitivity control 33. The adjusted signal is then split into a number of frequency channels 26 by the filter bank 34. Gains are applied to each channel 23 and the resulting signals are then passed through a non-linear loudness mapping function, called the Loudness Growth Function (LGF) 24. The LGF 24 maps the input dynamic range to the electrical dynamic range in a fashion that matches the loudness growth for electrical stimulation.

Figure 3:
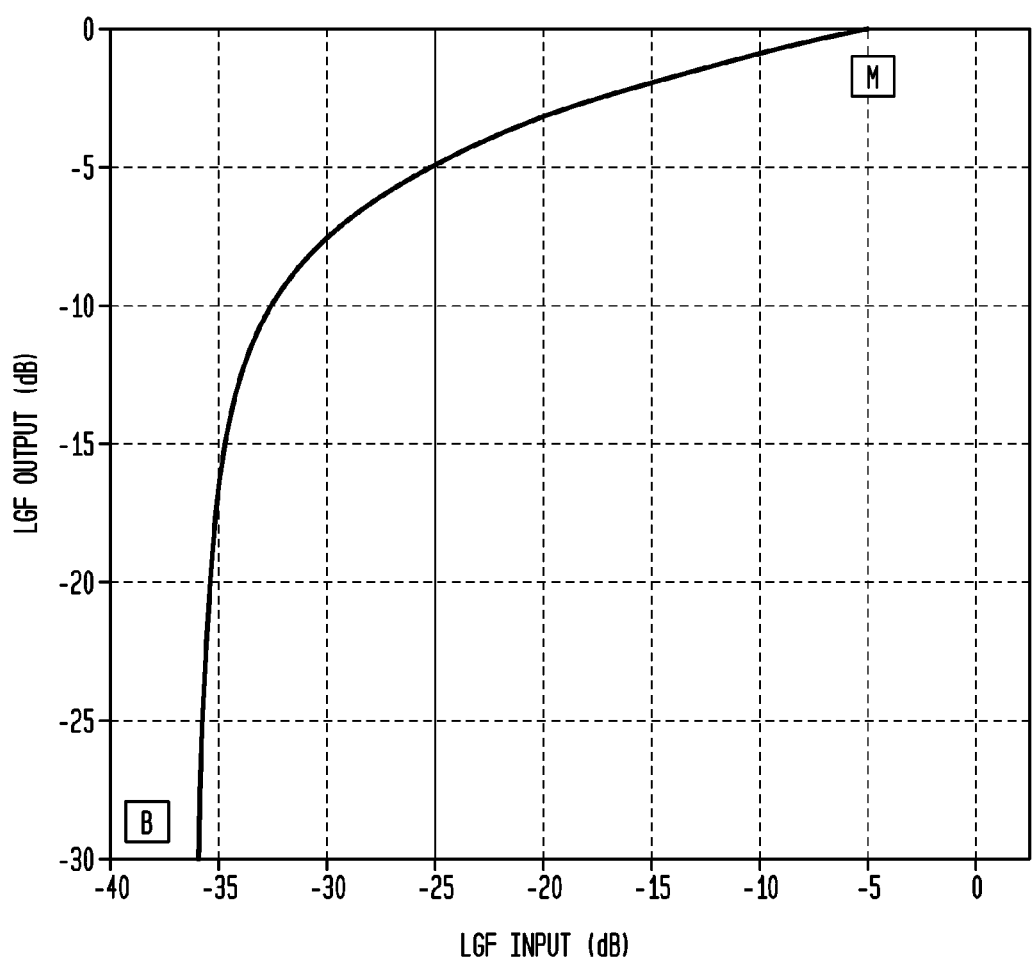
FIG. 3 shows a graphical representation of a loudness growth function.

An example of a typical LGF input/output curve is depicted in FIG. 3. The LGF is limited at the lower end by a point known as the base level (B). If the input level is below the base level, no signal is presented as stimulus. In alternative embodiments of the loudness growth function, the base level may represent a point in the function below which the output signal is strongly attenuated rather than cut-off completely. At the upper end, the LGF curve is limited by the maximum output level (M). Any input signal above this level is limited by the LGF curve to the maximum stimulus level.

Figure 4:
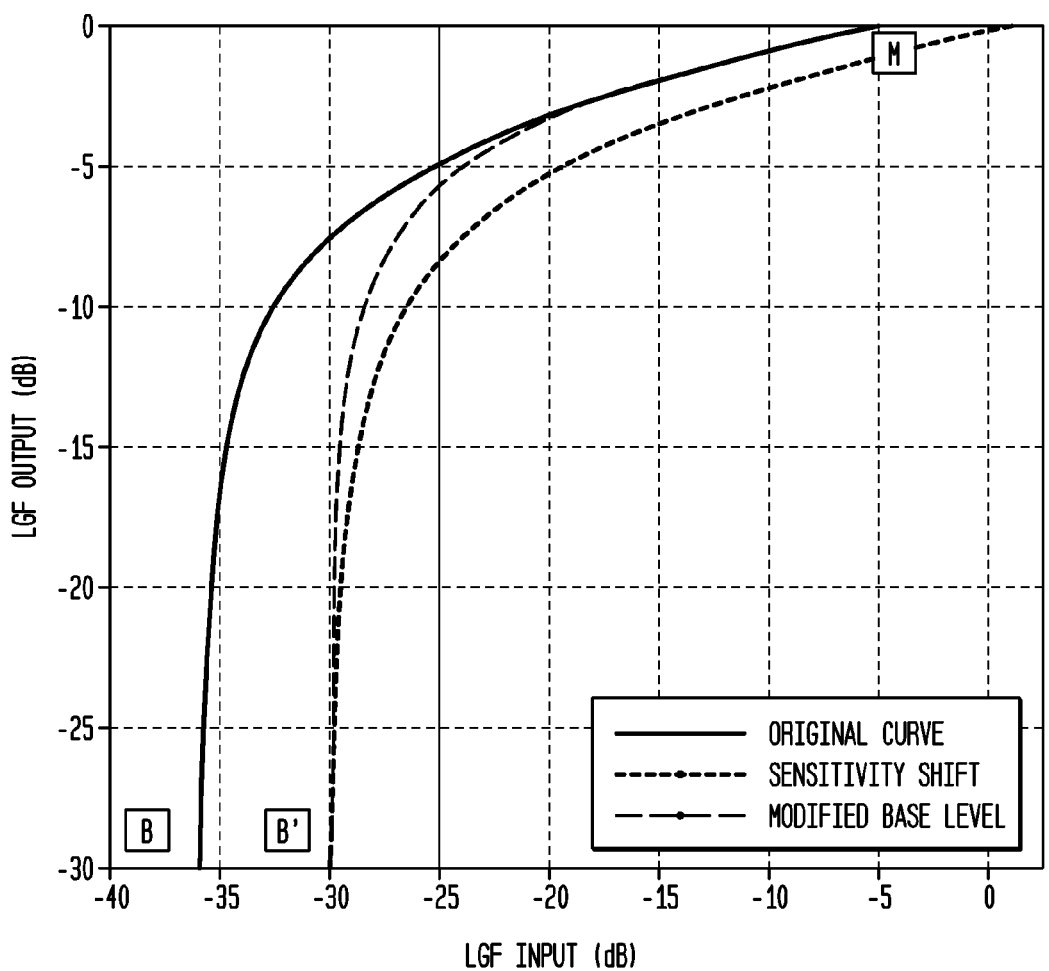
FIG. 4 shows a graphical representation of the approaches to modifying the dynamic range according to the methods shown schematically in FIG. 1.

One approach to reducing the effect of noise is to automatically adjust the sensitivity of the signal path such that the noise falls outside the output dynamic range. The effect of shifting the sensitivity in this way is depicted by the dashed curve in FIG. 4.

Consider a situation where the noise floor is at an input level of −30 dB and the current base level is at −36 dB. If the sensitivity is reduced by 6 dB it is as if the LGF curve has been shifted to the right by 6 dB. This has the effect of shifting the base level to B' such that the noise is now below the base level and is therefore not presented to the recipient. This procedure is performed by the ASC algorithm.

Such an approach has the negative side effect of mapping signals above the noise floor to a lower output level than before the sensitivity adjustment. For example, the input level that previously produced a maximum output level now produces an output that is less than maximum. For the recipient this means that it is harder to hear the portion of the target signal that is above the noise.

Instead of simply shifting the curve by applying attenuation, an implementation of the present invention modifies the input/output function such that the base level now coincides with the estimated noise floor (B'). Such a modification is depicted as the dash-dot curve in FIG. 4. This modification means that the noisy part of the input signal is removed from the output, but the maximum output level is reached by the same input level as before the modification.

Figure 5:
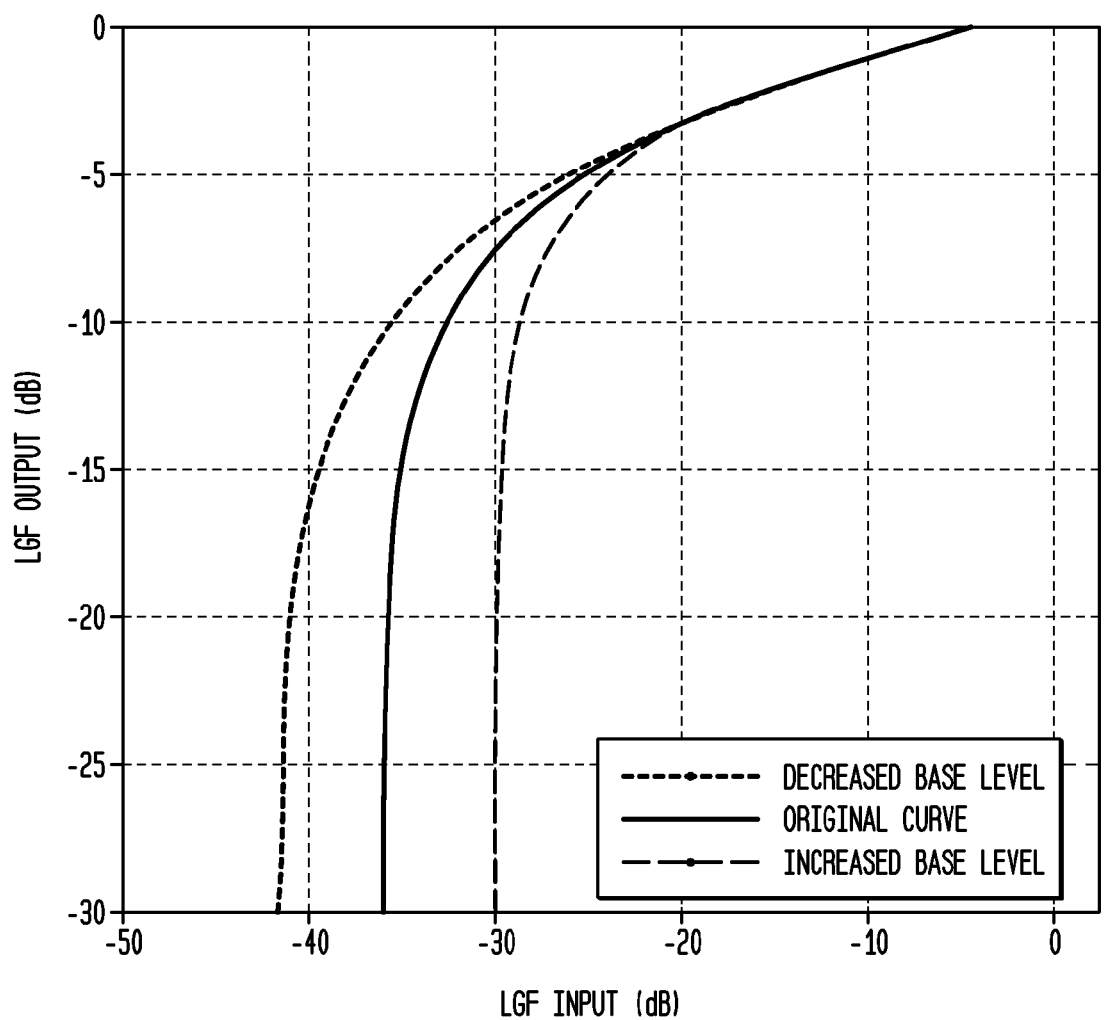
FIG. 5 shows a graphical representation of the effect of increasing or decreasing the dynamic range.

Note that this approach can also be applied in environments where the noise floor is low. In this case the base level may be reduced to allow more of the quiet sounds into the output dynamic range. The effect of increasing and decreasing the base level without modifying the maximum output level is shown graphically in FIG. 5.

Figure 6:
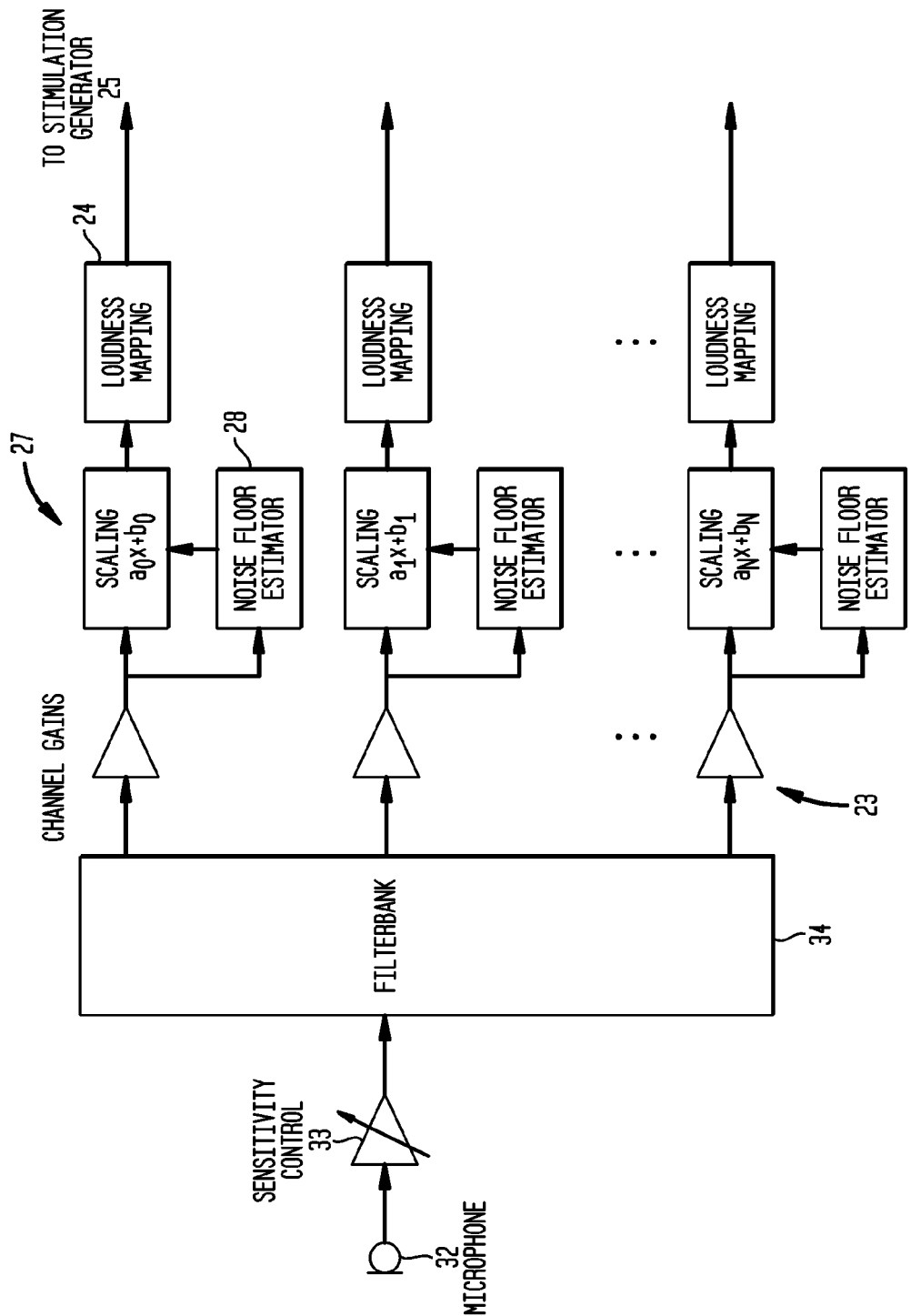
FIG. 6 shows a schematic of the signal path implemented under an embodiment of the present invention.

In the algorithm provided by the preferred implementation of the present invention, rather than modifying the loudness growth function directly, the algorithm pre-scales the input to the loudness growth function in response to a control signal. The purpose of the pre-scaling is to remap the input signal such that the noise floor of the environment is below/or at the base level. A pre-scaling is preferred to modifying the LGF due to the difficulty in reshaping the loudness growth function dynamically in a real-world implementation. In an alternative embodiment the loudness growth function may be modified directly rather than applying a pre-scaling. A signal path adapted to implement this aspect of the present invention is shown in FIG. 6.

This signal path incorporates a microphone 32, sensitivity control 33, filter bank 34, channel gain 23 and loudness mapping 24, as in the prior art. However, it also incorporates a new scaling block 27 before the loudness mapping block 24 on each channel, and a noise floor estimator 28 on each channel. The purpose of scaling block 27 is to rescale the signal such that the maximum output level (M) is unchanged, but the base level (B) of the LGF is modified (B') to follow the noise floor estimate.

Figure 7:
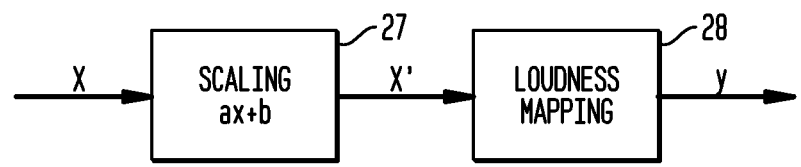
FIG. 7 shows a schematic of the signal path of FIG. 6, useful in determining the scaling parameters used to implement an embodiment of the invention.

For the purpose of deriving the scaling function parameters (a, b) it is helpful to define the intermediate signals (x, x' and y) shown in FIG. 7. x is the signal input to the scaling block 27; x' is the signal between the scaling block 27 and loudness mapping 28; and y is the signal output from the loudness mapping block 28 for further processing.

The loudness growth function is defined as follows:

$$y = \frac{\log\left(1 + \alpha \frac{x' - B}{M - B}\right)}{\log(1 + \alpha)}$$

Substituting in the equation of the scaling block to derive the above equation in terms of x:

$$y = \frac{\log\left(1 + \alpha \frac{(ax + b) - B}{M - B}\right)}{\log(1 + \alpha)}$$

At x=M we require the modified and unmodified output signals to be equal:

$$\frac{\log\left(1 + \alpha \frac{x - B}{M - B}\right)}{\log(1 + \alpha)} = \frac{\log\left(1 + \alpha \frac{(ax + b) - B}{M - B}\right)}{\log(1 + \alpha)}$$

which reduces to:

$M = aM + b$

At x=B' the output must go to zero so we have:

$$0 = \frac{\log\left(1 + \alpha \frac{(ax + b) - B}{M - B}\right)}{\log(1 + \alpha)}$$

which reduces to:

$B = aB' + b$

Combining these two results and solving for a we have:

$$a = \frac{B - M}{B' - M}$$

And then, $$b = M\left(1 - \frac{B - M}{B' - M}\right)$$

The scaling function is now defined in terms of the existing LGF parameters (B and M) and the desired base level (B').

The other component of the proposed algorithm is the noise floor estimator. The noise floor estimator controls the modification of the base level parameter, which is then used to derive the scaling parameters (a and b). Noise floor estimation is described in U.S. Pat. No. 6,151,400, incorporated by reference herein, is well known in the prior art, and accordingly will not be described in detail here.

Figure 10:
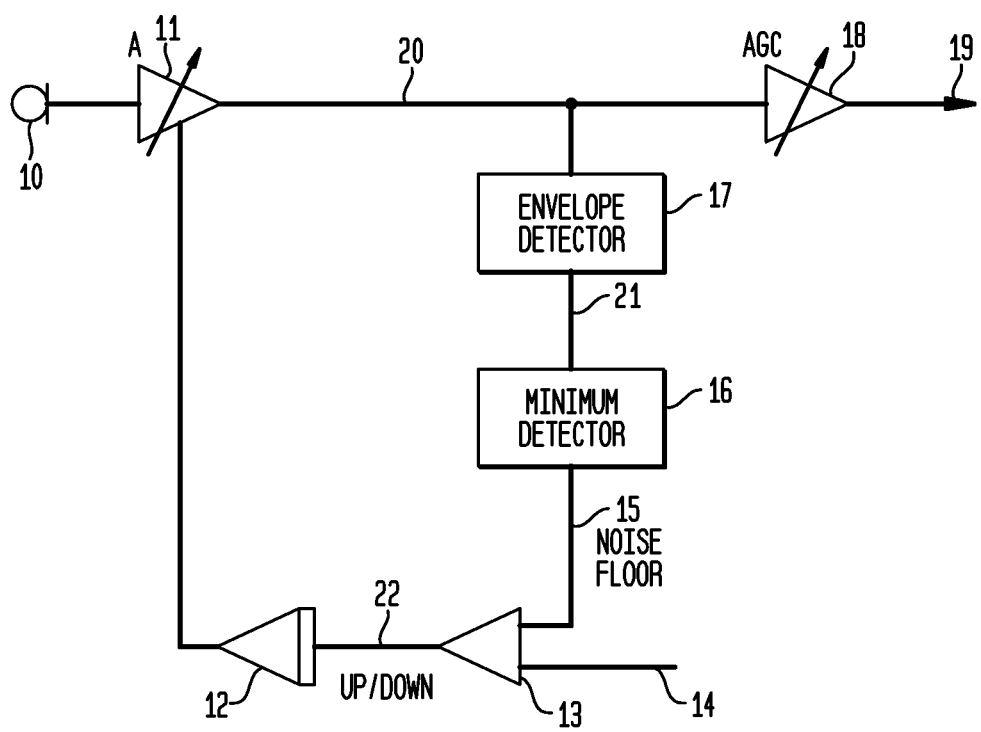
FIG. 10 shows an example of a prior art system.

Briefly, in U.S. Pat. No. 6,151,400 and as shown in FIG. 10, a signal is captured by microphone 10 and passed to a variable gain amplifier 11. The output of amplifier 10 is processed by an envelope detector 17 which rectifies the signal and applies a smoothing filter. The resulting envelope signal 21 is then processed by a minimum detector 16 which responds rapidly to any reduction in envelope amplitude signal and only gradually responds to increases. In this way the output of the minimum detector reflects the lowest signal amplitude over the preceding period. Typically, this period would be set by varying the time constant of minimum detector 16 to be several seconds. Thus, the minimum detector output 15 is an estimate of the noise floor. In this circuit, comparator 13 compares the noise floor signal 15 with a preset breakpoint, so as to control the gain of amplifier 11 via comparator 13 and integrator 12. However, for present purposes, it is only the noise floor estimator stage output which is required.

Figure 8:
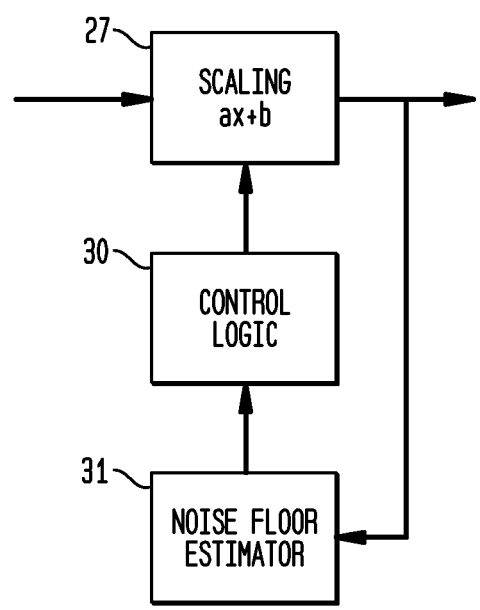
FIG. 8 shows a schematic of an alternative control arrangement.

According to implementations of the present invention, the noise floor estimate may be used to drive the desired base level directly as depicted in FIG. 6, so that the noise floor estimate is an input to scaling block 27, or it may be used indirectly. Such an alternate configuration is shown in FIG. 8. Note that in this arrangement the noise floor estimate is computed on the output of the scaling block rather than the input.

Figure 9:
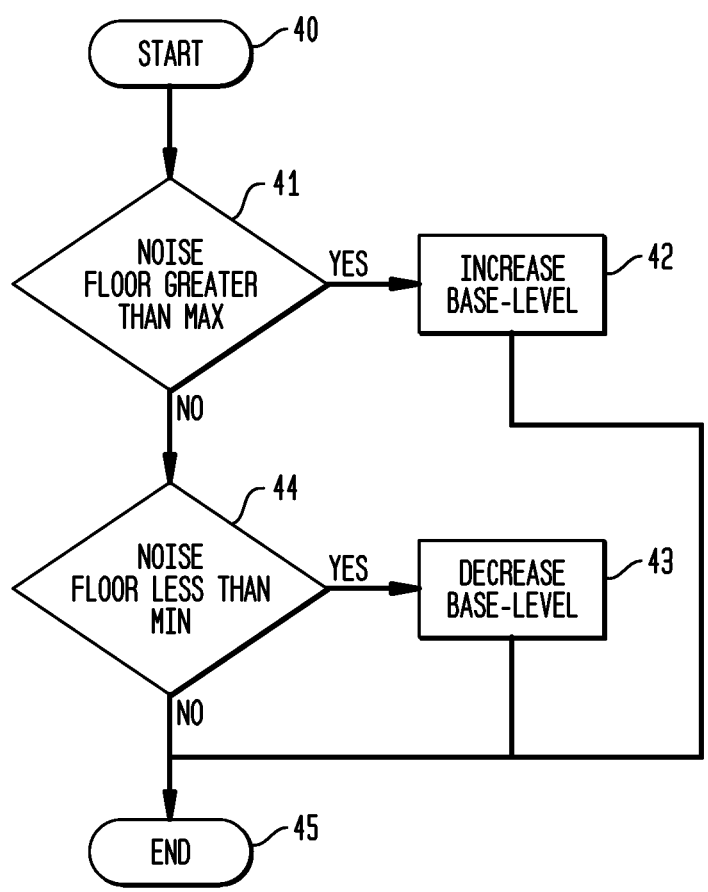
FIG. 9 shows a flow diagram of the control logic block of FIG. 8.

In this configuration the noise floor estimate is passed into a control logic block, which then determines how the base level should be adjusted. By decoupling the control signal from the adjustment of the dynamic range we can allow other requirements to be included in the algorithm. For example, it would then be possible to specify a maximum and minimum allowable dynamic range. A simple flow chart of an example control logic block is shown in FIG. 9.

If the noise floor is above an upper threshold (MAX) 41, then this means that the base level is too low and therefore allowing too much noise through the system. The control logic will respond to this by increasing the base level at block 42 (either by an additive or multiplicative factor). Eventually the base level will be increased enough that the noise floor is below the upper threshold and the algorithm can cease increasing the base level.

Similarly if the noise floor is below a second threshold (MIN), determined at block 44, then this implies that the base level is too high and cutting off some of the target signal. The control logic responds to this situation by decreasing the base level until the noise floor estimate is above the low threshold. When the noise floor estimate is between the two thresholds the control logic does not apply an adjustment to the base level, reaching end block 45.

The rate at which the base level is increased or decreased would be programmable and most the rate of increase and rate of decrease would be independent from each other. For example, the base level may be increased faster than it is decreased. This would cause the algorithm to weight cutting off noise more highly than allowing more signal through the signal path. Although this description has focused on using the estimated noise floor as the parameter used to generate the control signal various other parameters may be applicable, for example:

Energy estimate (e.g. RMS)
Amplitude histogram percentiles
Amplitude modulation depth For example, the modulation depth can be computed in a number of ways. One technique is to form a noise floor estimate (as mentioned in the ASC patent U.S. Pat. No. 6,151, 400). A signal peak estimate is then formed by changing the minimum detector to a maximum detector. These two values can then either be divided or alternatively subtracted in the log domain to determine the modulation depth.

This description has also focused on rescaling the signal with reference to the set points in the loudness growth function. However, it is also possible to use a similar rescaling method in systems that do not contain a loudness growth function. In this case other set points would need to be defined that mark important points in the dynamic range to be optimized.

This description has focused on performing the dynamic range adjustment on a number of frequency bands, in an alternative embodiment of this invention the algorithm may be implemented on the broadband audio signal. It will be appreciated that variations and additions are possible within the scope of the present invention.

The invention claimed is:

1. A method for processing an input sound signal by an auditory prosthesis comprising: performing a frequency analysis on the input sound signal to generate a plurality of analysis signals each corresponding to a channel within the input sound signal;
    applying a loudness growth function to each of the plurality of analysis signals;
    manipulating the output of the loudness growth function, in response to a control signal, such that, for each channel, a minimum output level of the channel is manipulated in response to the control signal, while a maximum output level of the channel remains substantially unchanged; and
    applying stimulation to a recipient based on the manipulated output of the loudness growth function.

2. The method of claim 1, wherein the control signal is derived, directly or indirectly, from one or more of estimated noise floor, energy estimate, amplitude histogram percentiles, and amplitude modulation depth.

3. The method according to claim 1, wherein the auditory prosthesis is a hearing aid, a cochlear prosthesis, or a hybrid electrical / acoustic stimulation device.

4. A method for processing an input signal in an auditory prosthesis to produce an output signal, said output signal having a maximum output level and a minimum output level, said method including at least the steps of:
    estimating the noise floor of the input signal;
    applying a loudness growth function to the input signal;
    manipulating the output of the loudness growth function such that a base level of the output signal is manipulated in response to the noise floor estimate, without substantially changing the maximum output level of the output; and
    applying stimulation to a recipient based on the manipulated output of the loudness growth function.

5. The method according to claim 4, wherein the base level of the manipulated output of the loudness growth function coincides substantially with the estimated noise floor.

6. The method according to claim 4, wherein the manipulating the output of the loudness growth function is based on one or more of the estimated noise floor, energy estimate, amplitude histogram percentiles, and amplitude modulation depth.

7. The method according to claim 6, wherein if the noise floor is above a predetermined upper threshold then the base level is increased and if the noise floor is below a predetermined lower threshold then the base level is decreased.

8. An apparatus for processing a sound signal in an auditory prosthesis to produce an output signal, said output signal having a maximum output level and a base level, comprising:
    a noise floor estimator for estimating a noise floor of the sound signal; and
    an adjustment circuit for applying a loudness growth function to the sound signal to provide an output signal;
    a manipulator circuit for manipulating the output signal of the loudness growth function such that a minimum output level of the output signal is manipulated in response to the noise floor estimate without substantially changing a maximum output level of the output signal.

9. The apparatus according to claim 8, wherein auditory prosthesis is a hearing aid, a cochlear prosthesis, or a hybrid acoustic/electric stimulation device.

10. A method for processing an input signal in an auditory prosthesis to produce an output signal, said method comprising:
    processing said input signal so as to produce a set of channel input signals corresponding to frequency channels;
    estimating, for each channel, a noise floor of the channel input signal;
    applying, for each channel, a loudness growth function to the channel input signal to produce a channel output signal, the channel output signal having a base level and a maximum output level;
    manipulating, for each channel, the output of the loudness growth function such that the base level of the channel output signal is manipulated in response to the noise floor estimate, while the maximum output level of the channel output signal remains substantially the same; and
    applying stimulation to a recipient using at least one of the channel output signals.

11. The method according to claim 10, wherein the base level of the channel output signal coincides substantially with the estimated noise floor for that channel.

12. The method according to claim 10, wherein the manipulating the output of the loudness growth function is based on one or more of the estimated noise floor, energy estimate, amplitude histogram percentiles, and amplitude modulation depth.

13. The method according to claim 10, wherein if the noise floor estimate is above a predetermined upper threshold, then the base level of the channel output signal is increased, and if the noise floor estimate is below a predetermined lower threshold then the base level of the channel output signal is decreased.

14. The method of claim 1, wherein the manipulating includes:
    applying a scaling function to each of the plurality of analysis signals in response to the control signal;
    the scaling function, for each channel, changing the minimum output level of the channel while leaving the maximum output level of the channel substantially unchanged; and
    providing the scaled analysis signals to the loudness growth function.

15. The method of claim 14, wherein, for each of the plurality of analysis signals, the applying a scaling function comprises:
    applying the formula y=ax+b to the analysis signal, where a and b are derived from an estimated noise floor, x is the analysis signal, and y is the scaled signal.

16. The method of claim 4, wherein:
    the applying and the manipulating are performed on a channel-by-channel basis; and
    the manipulating includes:
        applying a scaling function to the input signal;
        the scaling function, for each channel, changing the minimum output level of the channel while leaving the maximum output level of the channel substantially unchanged; and
        providing the channel-specific scaled signals to the loudness growth function.

17. The method of claim 16, wherein the applying a scaling function comprises:

applying, on a channel-by-channel basis, the formula y=ax+b to the input signal, where a and b are derived from an estimated noise floor, x is the input signal, and y is the scaled signal.

18. The apparatus of claim 16, wherein the manipulation circuit is further configured to apply the formula y=ax+b to the sound signal, where a and b are derived from an estimated noise floor, x is the sound signal, and y is the scaled signal.

19. The method of claim 10, wherein the manipulating includes:
   applying a scaling function to the channel input signals;
      the scaling function, for each channel, changing the minimum output level of the channel while leaving the maximum output level of the channel substantially unchanged; and
   providing the scaled channel input signals to the loudness growth function.

20. The method of claim 19, wherein the applying a scaling function comprises:
   applying the formula y=ax+b to each channel input signal, where a and b are derived from an estimated noise floor, x is the channel input signal, and y is the scaled signal.

21. The apparatus of claim 8, wherein:
   the adjustment circuit and the manipulation circuit are configured to operate on a channel-by-channel basis; and
   the manipulation circuit is further configured to:
      apply a scaling function to the input signal that, for each channel, changes the minimum output level of the channel while leaving the maximum output level of the channel substantially unchanged; and
      provide the channel-specific scaled signals to the adjustment circuit.

* * * * *